United States Patent [19]

Lerette

[11] Patent Number: 5,625,131
[45] Date of Patent: Apr. 29, 1997

[54] INBRED CORN LINE ZS0541

[75] Inventor: Raymond J. Lerette, Greeley, Colo.

[73] Assignee: Zenco (No. 4) Limited, London, England

[21] Appl. No.: 413,205

[22] Filed: Mar. 28, 1995

[51] Int. Cl.$^6$ .............................. A01H 1/02; A01H 4/00; A01H 5/00; C12N 5/04
[52] U.S. Cl. .................. 800/200; 800/250; 800/DIG. 56; 435/412; 47/58; 47/DIG. 1
[58] Field of Search .................................. 800/200, 205, 800/235, 250; 435/240.1, 240.4, 240.47, 240.49, 240.5; 47/58.01, 58.03, 58, DIG. 1

[56] References Cited

U.S. PATENT DOCUMENTS 5,436,388 7/1995 Eggerling et al. ....................... 800/200

OTHER PUBLICATIONS

Cole, E.H. and M.G. Neuffer. The Genetics of Corn, pg. 111.
Conger, B.V., F.J. Novak, R. Afza, and K. Erdelsky. "Somatic embryogenesis from cultured leaf segments of *Zea mays*", Plant Cell Reports, 6:345–347 (1987).
Duncan, D.R., M.E. Williams, B.E. Zehr and J.M. Widholm. "The production of callus capable of plant regeneration from immature embryos of numerous *Zea mays* genotypes", Planta, 165:322–332 (1985).
Edallo, et al., "Chromosomal Variation and Frequency of spontaneous Mutation Associated with in Vitro Culture and Plant Regeneration in Maize" Maydica XXVI, pp. 39–56 (1981).
Forsberg, R.A. and R.R. Smith. "Sources, Maintenance, and Utilization of Parental Material", Hybridization of Crop Plants, Chapter 4, pp. 65–81 (1980).
Green, C.E. and C.A. Rhodes. "Plant Regeneration in Tissue Cultures of Maize", Maize for Biological Research, pp. 367–372 (1982).
Hallauer, et al, "Corn Breeding", Corn and Corn Improvement pp. 463–564 (1988). Sprague et al, eds.
Lowe, Keith. Patent Application 0 160 390.
Meghji, M.R., J.W. Dudley, R.J. Lambert, and G.F. Sprague. "Inbreeding Depression, Inbred and Hybrid Grain Yields, and Other Traits of Maize Genotypes Representing Three Eras". Crop Science, vol. 24, pp. 545–549 (1984).
Phillips, et al., "Cell/Tissue Culture and In Vitro Manipulation", In Corn & Corn Improvement, 3rd Ed., ASA Publication, #18, pp. 345–349 & 356–357 (1988).
Poehlman, John Milton. *Breeding Field Crop*, AVI Publishing Company,Inc., Westport, Connecticut, pp. 237–246 (1987).
Rao, K.V., et al., "Somatic Embryogenesis in Glume Callus Cultures", Osmania University, Hyberabad, India.
Sass (1977) "Morphology.". In Corn & Corn Improvement. ASA Publication. Madison, WI, pp. 89–109.
Songstad, David D., David R. Duncan, and Jack M. Widholm. "Effect of 1–aminocyclopropane–1–carboxylic acid, silver nitrate, and norbornadiene on plant regeneration from maize callus cultures", Plant Cell Reports, 7:262–265 (1988).
Tomes, et al, "the Effect of Parental Genotype on Initiation of Embryogenic Callus from Elite Maize (Zea mays l.) Germplasm". Theor. Appl.Genet. 70., pp. 505–509. (1985).
Troyer, et al., "Selection for Early Flowering in Corn: 10 Late Synthetics". Crop Science, vol. 25, pp. 695–697 (1985).
Umbeck, et al. "Reversion of Male–Sterile T–Cytoplazm Maize to Male Fertility in Tissue Culture", Crop Science vol. 23, pp. 584–588 (1983).
Wright, H., "Commercial Hybrid Seed Production", Hybridization of Crop Plants, pp. 161–176, (1980).
Wych, R.D., "Production of Hybrid Seed Corn"; Corn and Corn Improvement, pp. 565–607 (1988).
Coe et al. 1988. *In* Corn and Corn Improvement. Third Edition. Sprague et al., eds. Am. Soc. Agronomy. pp.81–137.

*Primary Examiner*—Erich E. Veitenheimer
*Attorney, Agent, or Firm*—Dana Rewoldt

[57] ABSTRACT

Broadly this invention provides inbred corn line ZS0541. The methods for producing a corn plant by crossing the inbred line ZS0541 are encompassed by the invention. Additionally, the invention relates to the various parts of inbred ZS0541 including culturable cells. This invention relates to hybrid corn seeds and plants produced by crossing the inbred line ZS0541 with at least one other corn line.

10 Claims, No Drawings

INBRED CORN LINE ZS0541

FIELD OF THE INVENTION

This invention is in the field of corn breeding, specifically relating to an inbred corn line designated ZS0541.

BACKGROUND OF THE INVENTION

The original maize plant was indigenous to the Western Hemisphere. The plants were weedlike and only through the efforts of early breeders was a cultivated crop species developed. The physical traits of maize are such that self pollination or cross pollination can occur. Each plant has a separate male and female flower, the tassel and ear, respectively. Natural pollination occurs when wind transfers pollen from tassel to the silks on the corn ears. This type of pollination contributed to the wide variation of maize varieties present in the Western Hemisphere.

The development of a planned breeding program for maize only occurred in the last century. Originally, maize was an open pollinated variety having heterogeneous genotypes. The maize farmer selected uniform ears from the yield of these genotypes and reserved them for planting the next season. The result was a field of maize plants that were segregating for a variety of traits. This type of maize selection lead to at most incremental increases in seed yield.

Large increases in seed yield were the result of the development of hybrid corn varieties in planned breeding programs. Hybrids were developed by selecting corn lines and selfing these lines for several generations to develop homozygous pure inbred lines and crossing selected inbred lines with unrelated inbred lines to produce hybrid progeny (F1). Inbred lines can be difficult to produce since the inbreeding process in corn decreases the vigor. However, when two inbred lines are crossed, the hybrid plant evidences greatly increased vigor compared to open pollinated segregating maize plants. An important factor of the homozygosity and the homogeneity of the inbred lines is that the hybrid from any cross will always be the same, and can be reproduced.

The ultimate objective of the commercial maize seed companies is to produce high yielding, agronomically sound plants which perform well in certain regions or areas of the Corn Belt. To produce these types of hybrids, the companies must develop inbreds which carry needed traits into the hybrid combination. Hybrids are not uniformly adapted for the Corn Belt, but are specifically adapted for regions of the Corn Belt. Northern regions of the Corn Belt require shorter season hybrids than do southern regions of the Corn Belt. Hybrids that grow well in Colorado and Nebraska soils may not flourish in rich Illinois soil. Thus, a variety of major agronomic traits are important in hybrid combination for the various Corn Belt regions, and have an impact on hybrid performance.

Inbred line development and hybrid testing have been emphasized in the past half century in commercial maize production as a means to increase hybrid performance. Inbred development is usually done by pedigree selection. Pedigree selection can be selection in an $F_2$ population produced from a planned cross of two genotypes (often elite inbred lines), or selection of progeny of synthetic varieties, open pollinated, composite, or backcross populations. This type of selection is effective for highly inheritable traits, but other traits, for example, yield requires replicated test crosses at a variety of stages for accurate selection.

Maize breeders select for a variety of traits in inbreds that impact hybrid performance along with selecting for acceptable parental traits. Such traits include yield potential in hybrid combination; dry down; maturity; grain moisture at harvest; greensnap; resistance to root lodging; resistance to stalk lodging; grain quality; disease and insect resistance; ear and plant height; performance in different soil types such as: low level of organic matter, clay, sand, black, high pH, low pH; performance in: wet environments, drought environments, and no tillage conditions. These traits appear to be governed by a complex genetic system that makes selection and breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. Thus, the general procedure of producing a non segregating $F_1$ generation and self pollinating to produce a $F_2$ generation that segregates for traits does not easily lead to a useful inbred. Great care and breeder expertise must be used in selection of breeding material to continue to increase yield and agronomics of inbreds and resultant commercial hybrids.

SUMMARY OF THE INVENTION

The present invention relates to an inbred corn line ZS0541. Specifically, this invention relates to plants and seeds of this line. Additionally, this relates to a method of producing hybrid seed corn from this inbred. More particularly, this invention relates to the unique combination of traits that combine in corn line ZS0541.

Generally then, broadly the present invention includes an inbred corn seed designated ZS0541. This seed produces a corn plant.

The invention also includes the tissue culture of regenerable cells of ZS0541 wherein the tissue regenerates plants having the genotype of ZS0541. The tissue culture is selected from the group consisting of leaves, pollen, embryos, roots, root tips, anthers, silk, flowers, kernels, ears, cobs, husks and stalks, and cells and protoplasts thereof. The corn plant regenerated from ZS0541 having ZS0541's genotype.

The invention extends to hybrid seed produced by planting, in pollinating proximity, seeds of corn inbred lines ZS0541 and another inbred line; cultivating corn plants resulting from said planting; preventing pollen production by the plants of one of the inbred lines; allowing natural cross pollinating to occur between said inbred lines; and harvesting seeds produced on plants of the inbred. The hybrid seed produced by hybrid combination of plants of inbred corn seed designated ZS0541 and plants of another inbred line. Hybrid plants grown from this hybrid seed.

The invention further includes a method of hybrid F1 production. A first generation (F1) hybrid corn plant produced by the process of planting, in pollinating proximity, seeds of corn inbred lines ZS0541 and another inbred line; cultivating corn plants resulting from said planting; preventing pollen production by the plants of one of the inbred lines; allowing natural cross pollinating to occur between said inbred lines; harvesting seeds produced on plants of the inbred; and growing a harvested seed.

A tissue culture of the regenerable cells of hybrid plants produced with use of ZS0541 genetic material. A tissue culture of the regenerable cells of the corn plant produced by the method described above.

DEFINITIONS

In the description and examples which follow, a number of terms are used. In order to provide a clear and consistent understanding of the specifications and claims, including the scope to be given such terms, the following definitions are provided.

BL MOIST

The moisture percentage of the grain at black layer, ie, when 50% of the plants per plot have reached physiological maturity.

COLD GERM

Cold Germ is a measurement of seed germination under cold soil conditions. Data is reported as percent of seed germinating.

ECB

European corn borer a maize eating insect. ECBI is the first brood generation of European corn borers. ECBII is the second generation of European corn borers.

EMERGE

The number of emerged plants per plot (planted at the same seedling rate) collected when plants have two fully developed leaves.

GI

This is a selection index which provides a single quantitative measure of the worth of a hybrid based on four traits. Yield is the primary trait contributing to index values. The GI value is calculated by combining stalk lodging, root lodging, yield and dropped ears according to the attached mathematical formula:

$$GI=100+0.5 \text{ (YLD)}-0.9(\% \text{ STALK LODGE})-0.9(\% \text{ ROOT LODGE})-2.7(\% \text{ DROPPED EAR})$$

GLS

Grey Leaf Spot (*Cercospora Zeae*) disease rating. This is rated on a 1–9 scale with a "1" being very susceptible, and a "9" being very resistant.*

* Resistant—on a scale of 1–9 with 9 evidencing the trait most strongly: 1–2.9 ratings are susceptible, 3–5.9 ratings are intermediate, and 6–9 ratings are resistant.

GW

Goss' Wilt (*Corynebacterium nebraskense*). This is rated on a 1–9 scale with a "1" being very susceptible, and a "9" being very resistant.*

* Resistant—on a scale of 1–9 with 9 evidencing the trait most strongly: 1–2.9 ratings are susceptible, 3–5.9 ratings are intermediate, and 6–9 ratings are resistant.

HEATP10

The number of Growing Degree Units (GDU's) or heat units required for an inbred line or hybrid to have approximately 10 percent of the plants shedding pollen. This trait is measured from the time of planting. Growing Degree Units are calculated by the Barger Method where the GDU's for a 24 hour period are:

$$GDU = \frac{(Max\ Temp\ (°F.) - Min\ Temp\ (°F.))}{2} - 50$$

The highest maximum temperature used is 86° F. and the lowest minimum temperature used is 50° F. For each inbred or hybrid it takes a certain number of GDU's to reach various stages of plant development.

HEATBL

The number of GDU's after planting when approximately 50 percent of the inbred or hybrid plants in a plot have grain which has reached physiological maturity (black layer).

HEATPEEK

The number of GDU's after planting of an inbred when approximately 50 percent of the plants show visible tassel extension.

HEATP50

The number of GDU's required for an inbred or hybrid to have approximately 50 percent of the plants shedding pollen. Growing Degree Units are calculated by the Barger Method as shown in the HEATP10 definition.

HEATP90

The number of GDU's accumulated from planting when the last 100 percent of plants in an inbred or hybrid are still shedding enough viable pollen for pollination to occur. Growing Degree Units are calculated by the Barger Method as shown in the HEATP10 definition.

HEATS10

The number of GDU's required for an inbred or hybrid to have approximately 10 percent of the plants with silk emergence of at least 0.5 inches. Growing Degree Units are calculated by the Barger Method as shown in the HEATP10 definition.

HEATS50

The number of GDU's required for an inbred or hybrid to have approximately 50 percent of the plants with silk emergence of at least 0.5 inches. Growing Degree Units are calculated by the Barger Method as shown in the HEATP10 definition.

HEATS90

The number of GDU's required for an inbred or hybrid to have approximately 90 percent of the plants with silk emergence of at least 0.5 inches. Growing Degree Units are calculated by the Barger Method as shown in the HEATP10 definition.

$MDMV_A$

Maize Dwarf Mosaic Virus strain A. The cord is rated on a 1–9 scale with a "1" being very susceptible, and a "9" being very resistant.*

* Resistant—on a scale of 1–9 with 9 evidencing the trait most strongly: 1–2.9 ratings are susceptible, 3–5.9 ratings are intermediate, and 6–9 ratings are resistant.

$MDMV_B$

Maize Dwarf Mosaic Virus strain B. This is rated on a 1–9 scale with a "1" being very susceptible and a "9" being very resistant.*

* Resistant—on a scale of 1–9 with 9 evidencing the trait most strongly: 1–2.9 ratings are susceptible, 3–5.9 ratings are intermediate, and 6–9 ratings are resistant.

MOISTURE

The average percentage grain moisture of an inbred or hybrid at harvest time.

NLB

Northern Leaf Blight (*Exserohilum turcicum*) disease rating. This is rated on a 1–9 scale with a "1" being very susceptible, and a "9" being very resistant.*

* Resistant—on a scale of 1–9 with 9 evidencing the trait most strongly: 1–2.9 ratings are susceptible, 3–5.9 ratings are intermediate, and 6–9 ratings are resistant.

PCT TILLER

The total number of tillers per plot divided by the total number of plants per plot.

PLANT

This term includes plant cells, plant protoplasts, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

PLANT HEIGHT

The distance in centimeters from ground level to the base of the tassel peduncle.

RM

Predicted relative maturity based on the moisture percentage of the grain at harvest. This rating is based on known set of checks and utilizes standard linear regression analyses and is referred to as the Minnesota Relative Maturity Rating System.

SHED

The volume of pollen shed by the male flower rated on a 1–9 scale where a "1" is a very light pollen shedder, a "4.5" is a moderate shedder, and a "9" is a very heavy shedder. The Table(s) 3 have reduced the 1–9 shed scale to a 1–3 shed scale. Any shed on Table 3 can be multiplied by 3 to reach the 1–9 shed scale.

SLB

Southern Leaf Blight (*Bipolaris maydis*) disease rating. This is rated on a 1–9 scale with a "1" being very susceptible, and a "9" being very resistant.*

* Resistant—on a scale of 1–9 with 9 evidencing the trait most strongly: 1–2.9 ratings are susceptible, 3–5.9 ratings are intermediate, and 6–9 ratings are resistant.

TWT

The measure of the weight of grain in pounds for a one bushel volume adjusted for percent grain moisture.

VIGOR

Visual rating of 1 to 9 made 2–3 weeks post-emergence where a "1" indicates very poor early plant development, and a "9" indicates superior plant development.

WARM GERM

A measurement of seed germination under ideal (warm, moist) conditions. Data is reported as percent of seeds germinating.

YIELD (YLD)

Actual yield of grain at harvest adjusted to 15.5% moisture. Measurements are reported in bushels per acre.

% DROPPED EARS (DE)

The number of plants per plot which dropped their primary ear divided by the total number of plants per plot.

% LRG FLAT

Percentage by weight of shelled corn that passes through a $26/64$ inch round screen and a $14/64$ inch slot screen, but does not pass through a screen with $20.5/64$ inch round openings.

% LRG ROUND

Percentage by weight of shelled corn that passes through a $26/64$ inch round screen, but does not pass through a $14/64$ inch slot screen or a screen with $20.5/64$ inch round openings.

% MED FLAT

Percentage by weight of shelled corn that passes through a $20.5/64$ inch round screen and a $13/64$ inch slotted screen, but does not pass through a screen with $17/64$ inch round openings.

% MED ROUND

Percentage by weight of shelled corn that passes through a $20.5/64$ inch round screen, but does not pass through a $13/64$ inch slot screen or a screen with $17/64$ inch round openings.

% SML FLAT

Percentage by weight of shelled corn that passes through a $17/64$ inch round screen and a $12/64$ inch slotted screen, but does not pass through a screen with $15/64$ inch round openings.

% SML ROUND

Percentage by weight of shelled corn that passes through a $17/64$ inch round screen, but does not pass through a $12/64$ inch slotted screen or a screen with $15/64$ inch round openings.

% ROOT LODGE (RL)

Percentage of plants per plot leaning more that 30 degrees from vertical divided by total plants per plot.

% STALK LODGE (SL)

Percentage of plants per plot with the stalk broken below the primary ear node divided by the total plants per plot.

DETAILED DESCRIPTION OF THE INVENTION

ZS0541 is a very robust inbred which can be used as a male or female. ZS0541's cold germination results make use as a male the most frequent use. ZS0541 is characterized by excellent late season staygreen and plant integrity which is brought through into its hybrids. ZS0541 has excellent general combining ability. This general combining ability is increased when stiff stalk material is used as the female. ZS0541 has two visible characteristics which are: an extremely large tassel which sheds over longer than average time, and a red color in its stalks and leaves throughout the season. ZS0541 is best crossed to other inbreds with strong tendency to resist root lodging.

ZS0541 makes hybrids with top end yield and stability of yield. Hybrids are usually planted at about 31,000 resulting in a final stand of 28,000 to 29,000 plants per acre. Hybrids of ZS0541 are characterized by good plant health throughout the growing season and particularly excellent late season plant health. The drydown characteristic of ZS0541 hybrids are excellent. ZS0541 also carries the red coloring, the tassel size, and the tall stature into most hybrids.

The inbred ZS0541 has late season health and staygreen and plant integrity. This inbred is an excellent male or female parent. This inbred has a large tassel and visually shows a slightly red stalk color which may be linked to its ability to produce out West.

The inbred has shown uniformity and stability within the limits of environmental influence for all the traits as described in the Variety Description Information (Table 1) that follows. Most of the data in the Variety Description information was collected at Slater, Iowa.

The inbred has been self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in ZS0541.

The best method of producing the invention, ZS0541 which is substantially homozygous, is by planting the seed of ZS0541 which is substantially homozygous and self-pollinating or sib pollinating the resultant plant in an isolated environment, and harvesting the resultant seed or the resultant pollen.

TABLE 1

ZS0541
VARIETY DESCRIPTION INFORMATION

1  Type: Dent
2  Region Best Adapted: Northern and central region early-mid season
INBRED ZS0541

| #3 DAYS | MATURITY HEATUNITS | |
|---|---|---|
| 80 | 1514 | FROM PLANTING TO 50% OF PLANTS IN SILK |
| 80 | 1514 | FROM PLANTING TO 50% OF PLANTS IN POLLEN |
| 11 | | FROM 10% TO 90% POLLEN SHED |

| #4 DATA | PLANT | |
|---|---|---|
| 2 | | ANTHOCYANIN OF BRACE ROOTS: 1 = ABSENT 2 = FAINT 3 = MODERATE 4 = DARK |

| #5 COLOR/DATA | LEAF | |
|---|---|---|
| 3/DARK GREEN | | LEAF COLOR **MUNSELL CODE-5GY 3/4 |
| 3 | | LEAF SHEATH PUBESCENCE (1 = NONE TO 9 = PEACH FUZZ) |
| 4 | | MARGINAL WAVES (1 = NONE TO 9 = MANY) |
| 5 | | LONGITUDINAL CREASES (1 = NONE TO 9 = MANY) |

| #6 COLOR/DATA | TASSEL | |
|---|---|---|
| 6-8 | | POLLEN SHED (0 = STERILE TO 9 = HEAVY SHEDDER) |
| 5/GREEN-YELLOW | | ANTHER COLOR **MUNSELL CODE-2.5GY 8/8 |
| 2 w/17 | | GLUME COLOR **MUNSELL CODE-5GY 6/8 w/ 5R3/4 STRIPES |
| 2 | | BAR GLUME: 1 = ABSENT 2 = PRESENT |

| #7A COLOR/DATA | EAR (UNMUSKED DATA) | |
|---|---|---|
| 5/GREEN-YELLOW | | SILK COLOR (3 DAYS AFTER EMERGE) **MUNSELL CODE-2.5GY 8/10 NO CLOSE MATCH |
| 3/DARK GREEN | | FRESH HUSK (25 DAYS AFTER 50% SILK) **MUNSELL CODE-5GY 6/8 |
| 22/TAN | | DRY HUSK COLOR (65 DAYS AFTER 50% SILK **MUNSELL CODE-2.5Y 8/4 |
| 3 | | POSITION OF EAR AT DRY HUSK: 1 = UPRIGHT 2 = HORIZONTAL 3 = PENDENT |
| 2 | | HUSK TIGHTNESS (1 = VERY LOOSE TO 9 = VERY TIGHT) |
| 1 | | HUSK EXTENSION AT HARVEST: 1 = EXPOSED EAR 2 = 8 CM 3 = 8-10 CM 4 = >10 CM |

| #7B DATA | EAR (HUSKED DATA) | |
|---|---|---|
| 1 | | KERNEL ROWS: 1 = INDISTINCT 2 = DISTINCT |
| 1 | | ROW ALIGNMENT: 1 = STRAIT 2 = SLIGHT CURVE 3 = SPIRAL |
| 2 | | EAR TAPPER: 1 = STRAIT 2 = AVERAGE 3 = EXTREME |

| #8 COLOR/DATA | KERNEL (DRY) | |
|---|---|---|
| 1 | | ALEURONE COLOR PATTERN: 1 = HOMO 2 = SEG |
| 8/YELLOW-ORANGE | | ALEURONE COLOR **MUNSELL CODE-2.5Y 8/10 |
| 8/YELLOW-ORANGE | | HARD ENDOSPERM COLOR ***MUNSELL CODE-5Y 7/10 |
| 3 | | ENDOSPERM TYPE |
| 7/YELLOW | | CROWN COLOR **MUNSELL CODE-2.5Y 8/10 |

| #9 COLOR | COB | |
|---|---|---|
| 19/WHITE | | COB COLOR *MUNSELL CODE-WHITE |

COLOR CHOICES (Use in conjunction with Munsell color code to describe all color choices

| | | | | |
|---|---|---|---|---|
| 01 = Light Green | 06 = Pale Yellow | 11 = Pink | 16 = Pale Purple | 21 = Buff |
| 02 = Medium Green | 07 = Yellow | 12 = Light Red | 17 = Purple | 22 = Tan |
| 03 = Dark Green | 08 = Yellow-Orange | 13 = Cherry Red | 18 = Colorless | 23 = Brown |
| 04 = Very Dark Green | 09 = Salmon | 14 = Red | 19 = White | 24 = Bronze |
| 05 = Green-Yellow | 10 = Pink-Orange | 15 = Red & White | 20 = White Capped | 25 = Variegated (Describe) |
| | | | | 26 = Other (Describe) |

| #10 | N | MEAN | STD. | T-STAT | PROB | 95% CI |
|---|---|---|---|---|---|---|
| EAR HEIGHT(CM) | 15 | 66.87 | 6.25 | 41.40 | 0.0000 | (63.70, 70.03) |
| LENGTH OF PRIMARY EAR LEAF(CM) | 15 | 96.40 | 4.00 | 93.42 | 0.0000 | (94.38, 98.42) |
| WIDTH OF PRIMARY EAR LEAF(CM) | 15 | 7.97 | 0.48 | 64.20 | 0.0000 | (7.72, 8.21) |
| TOP EAR INTERNODE(CM) | 15 | 17.87 | 1.30 | 53.15 | 0.0000 | (17.21, 18.53) |
| DEGREE OF LEAF ANGLE | 15 | 33.33 | 2.55 | 50.54 | 0.0000 | (32.04, 34.63) |
| # OF EARS PER PLANT | 15 | 1.00 | 0.00 | | | (1.00, 1.00) |

TABLE 1-continued

| | | | | | | |
|---|---|---|---|---|---|---|
| # OF LEAVES ABOVE TOP EAR | 15 | 5.20 | 0.41 | 48.64 | 0.0000 | (4.99, 5.41) |
| # OF PRIMARY LATERAL TASSEL BRANCHES | 15 | 17.33 | 1.95 | 34.39 | 0.0000 | (16.35, 18.32) |
| PLANT HEIGHT(CM) | 15 | 166.8 | 5.94 | 108.7 | 0.0000 | (163.8, 169.8) |
| TASSEL LENGTH(CM) | 15 | 48.73 | 2.25 | 83.85 | 0.0000 | (47.59, 49.87) |
| TASSEL BRANCH ANGLE | 15 | 50.67 | 9.34 | 21.01 | 0.0000 | (45.94, 55.39) |
| # OF TILLER PER PLANTS | 15 | 0.00 | 0.00 | | | (0.00, 0.00) |
| WEIGHT PER 100 KERNELS(GM) | 15 | 24.93 | 4.43 | 21.81 | 0.0000 | (22.69, 27.17) |
| EAR LENGTH(CM) | 15 | 14.61 | 1.06 | 53.51 | 0.0000 | (14.07, 15.14) |
| EAR WEIGHT(GM) | 15 | 101.8 | 19.21 | 20.53 | 0.0000 | (92.13, 111.6) |
| # OF KERNEL ROWS | 15 | 16.00 | 0.76 | 81.98 | 0.0000 | (15.62, 16.38) |
| COB DIAMETER AT MID-POINT(MM) | 15 | 24.42 | 0.42 | 226.4 | 0.0000 | (24.21, 24.63) |
| EAR DIAMETER AT MID-POINT(MM) | 15 | 40.39 | 1.46 | 107.2 | 0.0000 | (39.66, 41.13) |
| KERNEL LENGTH(MM) | 15 | 10.32 | 0.64 | 61.97 | 0.0000 | (9.99, 10.65) |
| KERNEL THICKNESS(MM) | 15 | 5.40 | 0.62 | 33.93 | 0.0000 | (5.09, 5.71) |
| KERNEL WIDTH(MM) | 15 | 7.31 | 0.43 | 66.01 | 0.0000 | (7.10, 7.53) |
| % ROUND KERNELS(SHAPE GRADE) | 15 | 53.10 | 12.63 | 16.29 | 0.0000 | (46.71, 59.49) |
| SHANK LENGTH | 15 | 8.05 | 4.14 | 7.52 | 0.0000 | (5.95, 10.14) |

11 DISEASE RESISTANCE - Common corn rust = 7.3
  Northern leaf blight = 5
  Gray leaf spot = 6
  Maize dwarf mosaic virus strain B = 1
12 The inbreds for comparison to ZS0541 are similar in
  maturity or phenotype. These inbreds are PVP#9000065, ZS0193, A632,
  and SGI100.

The Munsell code is a reference book of color which is known and used in the industry and by persons with ordinary skill in the art of plant breeding.

The purity and homozygosity of inbred ZS0541 is constantly being tracked using isozyme genotypes as shown in Table 2.

Isozyme Genotypes for ZS0541

Isozyme data were generated for inbred corn line ZS0541 according to procedures known and published in the art. The data in Table 2 gives the electrophoresis data on ZS0541.

combination. ZS0541 data shows some of the important characteristics and traits.

Table 3A compares ZS0541 to PVP#000065. ZS0541 is higher yielding and has higher grain harvest moisture than PVP#000065. ZS0541 flowers later and has lower germination under warm and cold testing conditions than PVP#000065. ZS0541 has more seedling vigor and better seedling emergence than PVP#000065. ZS0541 is a taller plant with higher ear placement than PVP#000065. ZS0541 has better pollen shed and ear quality than does LH163 across three experiments.

TABLE 2

ELECTROPHORESIS RESULTS FOR ZS0541

| INBRED | ACP1 | ACP4 | ADH | MDH1 | MDH2 | PGD1 | PGD2 | PH1 | PGM | IDH2 |
|---|---|---|---|---|---|---|---|---|---|---|
| ZS0541 | 33 | 00 | 22 | 22 | 11 | 11 | 11 | 22 | 22 | 11 |

Inbred and Hybrid Performance of ZS0541

The traits and characteristics of inbred corn line ZS0541 are listed to compare with other inbreds and/or in hybrid

TABLE 3A

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVER- ALL | ZS0541 | 5.5 | 93.0 | | 182.0 | 76.2 | 2.5 | 2.8 | |
| | PVP#000065 | 5.3 | 78.9 | | 168.1 | 66.9 | 2.0 | 2.3 | |
| | # EXPTS | 3 | 3 | | 3 | 3 | 2 | 3 | |
| | DIFF | 0.2 | 14.1 | | 14.0 | 9.3 | 0.5 | 0.5 | |
| | PROB | 0.423 | 0.148 | | 0.229 | 0.162 | 0.500 | 0.225 | |

| YEAR | INBRED | HEATP10 | HEATP50 | HEATP90 | HEATS10 | HEATS50 | HEATS90 |
|---|---|---|---|---|---|---|---|
| OVER- ALL | ZS0541 | 1272 | 1316 | 1360 | 1295 | 1331 | 1367 |
| | PVP#000065 | 1239 | 1280 | 1325 | 1274 | 1315 | 1344 |
| | # EXPTS | 3 | 3 | 3 | 3 | 3 | 3 |
| | DIFF | 33 | 35 | 35 | 21 | 16 | 23 |
| | PROB | 0.237 | 0.097*** | 0.002* | 0.053*** | 0.187 | 0.202 |

TABLE 3A-continued

PAIRED INBRED COMPARISON DATA

| YEAR | INBRED | HEATPEEK | HEATBL | BL MOIST | % ROOT LODGE | % STALK LODGE | % DROPPED EARS | MOISTURE | YIELD |
|---|---|---|---|---|---|---|---|---|---|
| OVER-ALL | ZS0541 | 1222 | 2454 | 32.3 | | | | 10.1 | 70.8 |
| | PVP#000065 | 1195 | 2397 | 32.0 | | | | 9.5 | 58.2 |
| | # EXPTS | 3 | 1 | 1 | | | | 3 | 3 |
| | DIFF | 27 | 58 | 0.3 | | | | 0.5 | 12.6 |
| | PROB | 0.037** | | | | | | 0.450 | |

| YEAR | INBRED | WARM GERM | COLD GERM | % LRG ROUND | % LRG FLAT | % MED ROUND | % MED FLAT | % SML ROUND | % SML FLAT |
|---|---|---|---|---|---|---|---|---|---|
| OVER-ALL | ZS0541 | 92.0 | 87.0 | 11.2 | 10.6 | 33.9 | 32.0 | 6.6 | 4.5 |
| | PVP#000065 | 97.3 | 90.7 | 48.8 | 14.1 | 32.4 | 3.3 | 0.7 | 0.3 |
| | # EXPTS | 3 | 3 | 3 | 3 | 3 | 3 | 3 | 3 |
| | DIFF | 5.3 | 3.7 | 37.6 | 3.5 | 1.5 | 28.7 | 5.9 | 4.2 |
| | PROB | 0.408 | 0.494 | 0.019** | 0.141 | 0.058*** | | | |

Table 3B shows ZS0541 has higher yield by 20 bushels and higher grain harvest moisture than SGI100. ZS0541 reaches 10% pollination (HeatP10) and 50% pollination substantially later than SGI100, and ZS0541 reaches 10% silking (HeatS10, HeatS50, HeatS90) significantly earlier than SGI100. ZS0541 has lower germination in cold and warm test conditions than does SGI100, but ZS0541 has better seedling emergence than does SGI100. ZS0541 is a taller plant with higher ear placement and better ear quality than SGI100. ZS0541 also has better pollen shed than does SGI100.

Table 3C shows that ZS0541 and A632 have the same grain harvest moisture but ZS0541 has higher grain yield at harvest by 28 bushels than does A632. ZS0541 has lower germination under warm testing condition than A632 but higher germination under cold testing conditions. ZS0541 also shows significantly higher seedling vigor than does A632 and higher plant emergence. The two inbreds flower similarly. ZS0541 is a taller inbred with a slightly higher ear placement than A632. ZS0541 has better pollen shed and similar ear quality as does A632 across three experiments.

TABLE 3B

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVER-ALL | ZS0541 | 5.5 | 93.0 | | 182.0 | 76.2 | 2.5 | 2.8 | |
| | SGI100 | 5.7 | 90.6 | | 149.4 | 55.9 | 2.0 | 2.5 | |
| | # EXPTS | 3 | 3 | | 3 | 3 | 2 | 3 | |
| | DIFF | 0.2 | 2.4 | | 32.6 | 20.3 | 0.5 | 0.3 | |
| | PROB | 0.667 | 0.426 | | 0.064*** | 0.101 | 0.500 | 0.423 | |

| YEAR | INBRED | HEATP10 | HEATP50 | HEATP90 | HEATS10 | HEATS50 | HEATS90 |
|---|---|---|---|---|---|---|---|
| OVER-ALL | ZS0541 | 1272 | 1316 | 1360 | 1295 | 1331 | 1367 |
| | SGI100 | 1250 | 1300 | 1367 | 1338 | 1369 | 1400 |
| | # EXPTS | 3 | 3 | 3 | 3 | 3 | 3 |
| | DIFF | 23 | 16 | 7 | 42 | 38 | 32 |
| | PROB | 0.035** | 0.050** | 0.470 | 0.011** | 0.002* | 0.026** |

| YEAR | INBRED | HEATPEEK | HEATBL | BL MOIST | % ROOT LODGE | % STALK LODGE | % DROPPED EARS | MOISTURE | YIELD |
|---|---|---|---|---|---|---|---|---|---|
| OVER-ALL | ZS0541 | 1222 | 2454 | 32.3 | | | | 10.1 | 70.8 |
| | SGI100 | 1166 | 2487 | 31.0 | | | | 9.4 | 50.4 |
| | # EXPTS | 3 | 1 | 1 | | | | 3 | 3 |
| | DIFF | 56 | 33 | 1.3 | | | | 0.7 | 20.4 |
| | PROB | 0.089*** | | | | | | 0.257 | |

| YEAR | INBRED | WARM GERM | COLD GERM | % LRG ROUND | % LRG FLAT | % MED ROUND | % MED FLAT | % SML ROUND | % SML FLAT |
|---|---|---|---|---|---|---|---|---|---|
| OVER-ALL | ZS0541 | 92.0 | 87.0 | 11.2 | 10.6 | 33.9 | 32.0 | 6.6 | 4.5 |
| | SGI100 | 96.7 | 93.7 | 32.3 | 19.0 | 36.6 | 9.4 | 1.5 | 0.5 |
| | # EXPTS | 3 | 3 | 3 | 3 | 3 | 3 | 3 | 3 |
| | DIFF | 4.7 | 6.7 | 21.1 | 8.4 | 2.7 | 22.6 | 5.1 | 4.0 |
| | PROB | 0.423 | 0.441 | 0.003* | 0.254 | 0.510 | | | |

TABLE 3C

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVER-ALL | ZS0541 | 5.5 | 93.0 | | 182.0 | 76.2 | 2.5 | 2.8 | |
| | A632 | 4.5 | 79.8 | | 166.8 | 73.2 | 1.8 | 2.7 | |
| | # EXPTS | 3 | 3 | | 3 | 3 | 2 | 3 | |
| | DIFF | 1.0 | 13.1 | | 15.2 | 3.0 | 0.8 | 0.2 | |
| | PROB | 0.074*** | 0.160 | | 0.303 | 0.506 | 0.205 | 0.423 | |

| YEAR | INBRED | HEATP10 | HEATP50 | HEATP90 | HEATS10 | HEATS50 | HEATS90 |
|---|---|---|---|---|---|---|---|
| OVER-ALL | ZS0541 | 1272 | 1316 | 1360 | 1295 | 1331 | 1367 |
| | A632 | 1261 | 1303 | 1354 | 1317 | 1356 | 1397 |
| | # EXPTS | 3 | 3 | 3 | 3 | 3 | 3 |
| | DIFF | 11 | 13 | 6 | 22 | 25 | 29 |
| | PROB | 0.0355 | 0.235 | 0.402 | 0.308 | 0.356 | 0.337 |

| YEAR | INBRED | HEATPEEK | HEATBL | BL MOIST | % ROOT LODGE | % STALK LODGE | % DROPPED EARS | MOISTURE | YIELD |
|---|---|---|---|---|---|---|---|---|---|
| OVER-ALL | ZS0541 | 1222 | 2454 | 32.3 | | | | 10.1 | 70.8 |
| | A632 | 1155 | 2383 | 33.0 | | | | 10.1 | 41.9 |
| | # EXPTS | 3 | 1 | 1 | | | | 3 | 3 |
| | DIFF | 67 | 72 | 0.8 | | | | 0.0 | 28.9 |
| | PROB | 0.122 | | | | | | | 0.970 |

| YEAR | INBRED | WARM GERM | COLD GERM | % LRG ROUND | % LRG FLAT | % MED ROUND | % MED FLAT | % SML ROUND | % SML FLAT |
|---|---|---|---|---|---|---|---|---|---|
| OVER-ALL | ZS0541 | 92.0 | 87.0 | 11.2 | 10.6 | 33.9 | 32.0 | 6.6 | 4.5 |
| | A632 | 98.5 | 86.8 | 6.4 | 4.9 | 51.5 | 25.3 | 8.7 | 2.4 |
| | # EXPTS | 3 | 3 | 3 | 3 | 3 | 3 | 3 | 3 |
| | DIFF | 6.5 | 0.2 | 4.8 | 5.7 | 17.6 | 6.8 | 2.1 | 2.1 |
| | PROB | 0.306 | 0.974 | 0.387 | 0.066*** | 0.055*** | | | |

Table 3D has only limited data but it does show that ZS0541 has lower grain harvest moisture than does ZS0193. ZS0541 has lower grain yield at harvest than does ZS0193. ZS0541 shows better emergence than ZS0193 in a single experiment.

TABLE 3D

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVER-ALL | ZS0541 | 6.0 | 72.2 | | 167.0 | 64.1 | 3.0 | | |
| | ZS0193 | | 52.2 | | | | | | |
| | # EXPTS | | 1 | | | | | | |
| | DIFF | | 20.0 | | | | | | |
| | PROB | | | | | | | | |

| YEAR | INBRED | HEATP10 | HEATP50 | HEATP90 | HEATS10 | HEATS50 | HEATS90 |
|---|---|---|---|---|---|---|---|
| OVER-ALL | ZS0541 | 1446 | 1481 | 1569 | 1459 | 1489 | 1538 |
| | ZS0193 | | | | | | |
| | # EXPTS | | | | | | |
| | DIFF | | | | | | |
| | PROB | | | | | | |

| YEAR | INBRED | HEATPEEK | HEATBL | BL MOIST | % ROOT LODGE | % STALK LODGE | % DROPPED EARS | MOISTURE | YIELD |
|---|---|---|---|---|---|---|---|---|---|
| OVER-ALL | ZS0541 | 1357 | 2541 | 20.5 | 0.0 | 0.0 | 0.0 | 9.1 | 35.1 |
| | ZS0193 | | | | 0.2 | 0.0 | 0.2 | 11.0 | 57.6 |
| | # EXPTS | | | | 1 | 1 | 1 | 1 | 1 |
| | DIFF | | | | 0.2 | 0.0 | 0.2 | 1.9 | 22.5 |
| | PROB | | | | | | | | |

| YEAR | INBRED | WARM GERM | COLD GERM | % LRG ROUND | % LRG FLAT | % MED ROUND | % MED FLAT | % SML ROUND | % SML FLAT |
|---|---|---|---|---|---|---|---|---|---|
| OVER-ALL | ZS0541 | | | 3.2 | 10.6 | 31.4 | 38.1 | 6.5 | 6.8 |

TABLE 3D-continued

| | | PAIRED INBRED COMPARISON DATA | | | | | |
|---|---|---|---|---|---|---|---|
| ALL | ZS0193 | 26.8 | 35.2 | 22.0 | 13.1 | 1.0 | 0.7 |
| | # EXPTS | 1 | 1 | 1 | 1 | 1 | 1 |
| | DIFF | 23.7 | 24.6 | 9.5 | 25.0 | 5.5 | 6.1 |
| | PROB | | | | | | |

Table 4 compares ZS0541 in hybrid combination to 8692 hybrid commercially available from ICI Seeds. Both hybrids contain a common tester.

TABLE 4

| HYBRID | YEAR | TESTS | GI | ADV | FI | ADV | YLD | ADV | MOIST |
|---|---|---|---|---|---|---|---|---|---|
| ZS0541/CT RE | 92–94 | 30 | 157 | 0 | 100 | 8 | 120.1 | 2.4 | 24.8 |
| 8692 RE | 92–94 | 30 | 157 | | 92 | | 117.6 | | 27.9 |

| HYBRID | ADV | SL | ADV | RL | ADV | DE | ADV | TWT | ADV |
|---|---|---|---|---|---|---|---|---|---|
| ZS0541/CT RE | 3.0* | 2.6 | –0.6 | 0.4 | –0.1 | 0.0 | 0.1 | 49.0 | –0.4 |
| 8692 RE | | 2.1 | | 0.2 | | 0.1 | | 49.5 | |

The following conditions are met:
1. The comparison was made in at least two of the three years.
2. FIVE OR MORE 1994 STRIP TESTS/RESEARCH HAVE THE COMPARISON.
3. THE 92–94 MOIST DIFFERENCE IS BETWEEN –4 AND 4.
NOTE: The * beside the MOIST ADV and the YIELD ADV denotes significance at the .10 level.

The comparison shows that on the common tester ZS0541 brings more yield advantage and a significant decrease in moisture of grain at harvest to the hybrid package when compared with 8692 having the same common tester.

occurs. The interpretation of the data for all traits is that a positive comparison is a practical advantage. A negative comparison is a practical disadvantage. The general combining ability of an inbred is clearly evidenced by the results

TABLE 5

| | ECB1 | | ECB2 | | ECB TUNNELLING | |
|---|---|---|---|---|---|---|
| INBRED | VISUAL RATING | # YEARS TESTED | STANDARD RATING | # YEARS TESTED | cm OF TUNNELLING | # YEARS TESTED |
| ZS0541 | 5.2 | 3 | 4.7 | 3 | 56.6 | 3 |
| ZS0193 | 5.3 | 2 | 2.8 | 2 | 21.5 | 2 |
| A632 | 5.3 | 8 | 5.5 | 8 | 14.6 | 7 |

ZS0541 has a similar ECBI rating as does ZS0193 and A632. ZS0541 brings a nice 4.7 ECBII rating to the package. In comparison ZS0193 only has a 2.8 ECBII rating; however, A632 has a 5.5 ECBII rating.

of the general combining ability estimates. This data compares the inbred parent in a number of hybrid combinations to a group of "checks". The check data is from other companies' hybrids, particularly the leader in the industry

TABLE 6A

| | N | YM | GI | YLD | MOIST | % SL | % RL | % DE | RM |
|---|---|---|---|---|---|---|---|---|---|
| ZS0541 | 3866 | 0.2 | –0.5 | –0.1 | 0.6 | 0.2 | –0.7 | 0.0 | 107 |
| Hybrid #243 | | | | | | | | | |
| PVP#000065 | 1033 | –0.1 | –3.4 | –7.6 | 1.0 | 0.9 | –0.5 | 0.0 | 98 |
| Hybrid #102 | | | | | | | | | |
| A632 | 213 | –0.3 | –2.9 | –4.4 | –0.3 | 0.1 | –0.6 | 0.0 | 98 |
| Hybrid #13 | | | | | | | | | |
| ZS0193 | 85 | –0.2 | 1.2 | 1.9 | –1.0 | 0.2 | 0.1 | 0.0 | 101 |
| Hybrid #14 | | | | | | | | | |
| SGI100 | 4199 | 0.1 | 1.1 | 1.6 | 0.2 | 0.0 | 0.5 | –0.1 | 110 |
| Hybrid #164 | | | | | | | | | |

Table 6A shows the GCA (general combining ability) estimate of ZS0541 compared with the GCA estimates of the and ICI Seeds' commercial products and pre-commercial hybrids which were grown in the same sets and locations.

Table 6A compares ZS0541 in hybrid combination with the comparable inbreds in hybrid combinations across a variety of different hybrid combinations. These hybrid combinations differ but the data gives information on the versatility and strengths and weaknesses of the inbred across agronomic and yield and moisture traits.

ZS0541 evidences better yield by moisture than does PVP#000065, A632, or SGI100. ZS0541's G index rating is higher than PVP#000065 and A632 and lower than ZS0193 and SGI100 rating. The lower rating appears to be from ZS0541's root lodging data. ZS0541 yields better than PVP#000065 and A632 on average in hybrid combination. ZS0541 has lower yield than SGI100 and ZS0193, but ZS0541 has a higher grain moisture at harvest rating than does SGI100, ZS0193 or A632. ZS0541 has similar or better ratings for resistance to stalk lodging than does A632, ZS0193, SGI100 but lower ratings than PVP#000065. ZS0541 has the lowest root lodging of the four comparison inbreds in hybrid combination and similar ratings for dropped ear with A632, ZS0193, PVP#000065 but a higher rating than SGI100.

the experimental hybrids as an average. ZS0541 shows a higher rating for moisture at grain harvest (this indicates that ZS0541 has lower moisture) than does SGI100. Additionally, ZS0541 has better ratings for resistance to stalk lodging and for resistance to dropping an ear than SGI100.

TABLE 7

| YIELD RESPONSE | | | | | |
|---|---|---|---|---|---|
| HYBRIDS | YIELD | | | | |
| Environment | 136 | 154 | 172 | 190 | 208 |
| ZS0541/hybrid combination 1 | 141 | 158 | 175 | 192 | 210 |
| ZS0541/hybrid combination 2 | 149 | 165 | 182 | 199 | 215 |

Table 7 shows that in the first hybrid combination 1, ZS0541 yields better than the environment in low, medium and high yielding conditions. But in this hybrid combination, ZS0541 is particularly aggressive in low to low-medium yielding environments. A similar response is shown by ZS0541 in the second hybrid combination. Some

TABLE 6B

| | N | YM | GI | YLD | MOIST | % SL | % RL | % DE | RM |
|---|---|---|---|---|---|---|---|---|---|
| ZS0541 Hybrid #157 | 3085 | 0.2 | 0.2 | 0.9 | 0.5 | 0.3 | −0.6 | 0.0 | 108 |
| SGI100 Hybrid #96 | 3717 | 0.2 | 2.0 | 3.5 | 0.0 | 0.0 | 0.5 | −0.1 | 111 |

Table 6B compares ZS0541 in hybrid combination with stiff stalk material, with SGI100 in hybrid combination with stiff stalk material. Comparison of the ZS0541 data in Table 6A and 6B shows that both SGI100 and ZS0541 seem to have better ratings across the board if only shown in combinations containing stiff stalk inbreds for the cross.

ZS0541 has the same yield by moisture rating as does SGI100, a lower GI and a lower yield, though with stiff stalk ZS0541 gets a better performance than the commercials and additional data indicates that ZS0541 may excel in high yielding conditions also.

TABLE 8A

| HYBRID | YEAR | TESTS | GI | ADV | FI | ADV | YLD | ADV |
|---|---|---|---|---|---|---|---|---|
| ZS0541/INBRED 1RE | 92–94 | 139 | 178 | 3 | 126 | 4 | 162.8 | 7.6* |
| 8574 RE | 92–94 | 139 | 175 | | 122 | | 155.1 | |
| ST | 92–94 | 116 | 186 | 4 | 144 | 2 | 178.8 | 3.1* |
| ST | 92–94 | 116 | 182 | | 142 | | 175.6 | |
| ZS0541/INBRED 2RE | 92–94 | 85 | 178 | 2 | 126 | 4 | 166.2 | 10.2* |
| 8574 RE | 92–94 | 85 | 176 | | 123 | | 156.0 | |
| ST | 92–94 | 58 | 187 | 5 | 147 | 3 | 183.6 | 6.3* |
| ST | 92–94 | 58 | 182 | | 144 | | 177.3 | |

| HYBRID | MOIST | ADV | SL | ADV | RL | ADV | DE | ADV |
|---|---|---|---|---|---|---|---|---|
| ZS0541/INBRED 1RE | 22.3 | 0.5* | 2.1 | 0.0 | 1.6 | −1.4 | 0.1 | 0.1 |
| 8574 RE | 22.9 | | 2.2 | | 0.2 | | 0.1 | |
| ST | 18.2 | −0.5* | 2.3 | 1.1 | 1.0 | −0.4 | 0.1 | 0.5 |
| ST | 17.7 | | 3.5 | | 0.6 | | 0.6 | |
| ZS0541/INBRED 2RE | 22.4 | 9.4 | 2.9 | 0.1 | 3.1 | −2.9 | 0.1 | −0.1 |
| 8574 RE | 22.7 | | 2.1 | | 0.2 | | 0.1 | |
| ST | 17.3 | −0.7* | 4.1 | 0.2 | 1.2 | −0.2 | 0.2 | 0.4 |
| ST | 16.6 | | 4.3 | | 1.0 | | 0.6 | |

The following conditions are met:
1. The comparison was made in at least two of the three years.
2. FIVE OR MORE 1994 STRIP TESTS/RESEARCH HAVE THE COMPARISON.
3. THE 92–94 MOIST DIFFERENCE IS BETWEEN −4 AND 4.
NOTE: The * beside the MOIST ADV and the YIELD ADV denotes significance at the .10 level.

Table 8A shows ZS0541 in two different hybrid combinations against ICI Seeds' hybrid 8574. The RE data is research plots, the ST data is experimental strip plots. ZS0541/Inbred 1 shows in the RE data a better GI rating. ZS0541/Inbred 1 also had a significant yield advantage and grain moisture at harvest advantage over 8574. In the ST data, ZS0541/Inbred 1 had significantly better yield, significantly lower moisture and a better GI rating than 8574.

ZS0541/Inbred 2 was also compared against 8574 in RE and ST experiments. This data shows ZS0541/Inbred 2 had a significantly higher yield of 10.2 bushels per acre beyond 8574 and lower grain moisture at harvest. In the strip trials, ZS0541/Inbred 2 had a significantly higher yield and a significantly lower grain moisture at harvest than did 8574. ZS0541/Inbred 2 also had a higher G Index rating than 8574 had.

ZS0541/Inbred 1 can tolerate western soil especially when placed under irrigation. In the irrigated data, ZS0541 shows six bushels better yield and significantly lower grain moisture at harvest in research plots. In experimental strip trials, the yield is significantly better than 8574 by 5 bushels with significantly higher grain moisture at harvest than 8574. When compared to all environments the ZS0541 hybrid appears to flourish in the West under irrigation.

TABLE 8B

| HYBRID | YEAR | TESTS | GI | ADV | FI | ADV | YLD | ADV |
|---|---|---|---|---|---|---|---|---|
| (All) | | | | | | | | |
| ZS0541/INBRED1 RE | 92–94 | 139 | 178 | 3 | 126 | 4 | 162.8 | 7.6* |
| 8574 RE | 92–94 | 139 | 175 | | 122 | | 155.1 | |
| ST | 92–94 | 116 | 186 | 4 | 144 | 2 | 178.8 | 3.1* |
| ST | 92–94 | 116 | 182 | | 142 | | 175.6 | |
| (IRR West) | | | | | | | | |
| ZS0541/INBRED1 RE | 92–94 | 8 | 174 | 1 | 121 | 4 | 154.0 | 6.4 |
| 8574 RE | 92–94 | 8 | 173 | | 117 | | 146.7 | |
| ST | 92–94 | 47 | 192 | 5 | 153 | 2 | 188.7 | 5.2* |
| ST | 92–94 | 47 | 187 | | 151 | | 183.5 | |

| HYBRID | MOIST | ADV | SL | ADV | RL | ADV | DE | ADV |
|---|---|---|---|---|---|---|---|---|
| (All) | | | | | | | | |
| ZS0541/INBRED1 RE | 22.3 | 0.5* | 2.1 | 0.0 | 1.6 | −1.4 | 0.1 | 0.1 |
| 8574 RE | 22.9 | | 2.2 | | 0.2 | | 0.1 | |
| ST | 18.2 | −0.5* | 2.3 | 1.1 | 1.0 | −0.4 | 0.1 | 0.5 |
| ST | 17.7 | | 3.5 | | 0.6 | | 0.6 | |
| (IRR West) | | | | | | | | |
| ZS0541/INBRED1 RE | 23.1 | 1.1* | 1.0 | −0.3 | 2.1 | −1.9 | 0.0 | 0.0 |
| 8574 RE | 24.3 | | 0.7 | | 0.2 | | 0.0 | |
| ST | 16.5 | −0.8* | 3.1 | 1.0 | 0.4 | 0.5 | 0.0 | 0.2 |
| ST | 15.7 | | 4.1 | | 0.9 | | 0.2 | |

The following conditions are met:
1. The comparison was made in at least two of the three years.
2. FIVE OR MORE 1994 STRIP TESTS/RESEARCH HAVE THE COMPARISON.
3. THE 92–94 MOIST DIFFERENCE IS BETWEEN −4 AND 4.
NOTE: The * beside the MOIST ADV and the YIELD ADV denotes significance at the .10 level.

Table 8B compares ZS0541/Inbred 1 across all environments with the ZS0541/Inbred 1 in the West (having low organic material in the soil) in irrigated conditions. Clearly,

TABLE 9A

HYBRID SUMMARY
ZS0541/INBRED 1

PERFORMANCE DATA

| | HYBRID | N | FI | GI | YM | YLD | MST | % SL | % RL | % DE |
|---|---|---|---|---|---|---|---|---|---|---|
| RE | 8570 | 72 | 5.3 | 2.9 | 0.4 | 4.8 | 1.0 | 0.0 | 0.1 | 0.1 |
| ST | 8570 | 4 | 3.8 | 2.5 | 0.6 | 7.1 | 0.6 | −1.1 | 0.0 | 0.0 |
| RE | 8543 | 79 | 10.1 | 3.1 | 0.9 | 5.0 | 3.1 | 0.8 | −0.2 | −0.0 |
| ST | 8543 | 5 | 12.1 | 7.2 | 1.0 | −1.1 | 3.3 | 3.3 | 0.0 | 0.0 |

Table 9A shows the advantage that ZS0541/Inbred 1 has over ICI Seeds' hybrid 8570 and 8543. ZS0541 in hybrid combination has better yield, yield by moisture, moisture, resistance to root lodging and dropped ears in both research and experimental strip testing than does hybrid 8570. ZS0541 in hybrid combination also evidences a better G index, yield by moisture, moisture than does 8543 in both research testing and experimental strip testing. In the research testing the yield advantage was five bushels per acre, in the strip experiments the yield had a −1.1 disadvantage. However, the ZS0541 hybrid had a grain moisture at harvest advantage of 3.3 over 8543.

8501. The ZS0541 hybrid has excellent resistance for head smut, the other hybrids are not rated. ZS0541 also shows intermediate resistance to common corn rust and northern leaf blight with an intermediate resistance to gray leaf spot. Resistance levels to GLS of 8501 and 8543 are higher, but in a similar range as the ZS0541 inbred. 8501 and 8543 are more resistant to northern leaf blight than is ZS0541.

TABLE 9B

HYBRID SUMMARY ZS0541/INBRED 1

AGRONOMIC DATA

| HYBRID | N | ESTAND | VIGOR | EAR HEIGHT | PLANT HEIGHT | PCTTIL | STAY GREEN | HEAT-P50 | HEAT-S50 | HEATBL |
|---|---|---|---|---|---|---|---|---|---|---|
| 8574 | 10 | −1.3 | 0.3 | 6.2 | 9.4 | −1.1 | 1.8 | 37.1 | 33.0 | 10.8 |
| 8570 | 10 | −0.8 | 0.9 | 1.7 | 3.1 | 1.9 | 0.0 | 3.3 | 4.9 | 6.5 |
| 8543 | 10 | −3.9 | 0.8 | 0.4 | 2.4 | 6.6 | 0.5 | −8.4 | −12.4 | −19.7 |

The advantage of ZS0541/Inbred when compared to 8574, 8570, 8543 is shown in Table 9B. Clearly ZS0541/Inbred 1 shows better vigor, better or similar stay green than do the comparison hybrids.

TABLE 9C

HYBRID SUMMARY ZS0541/INBRED 2

PERFORMANCE DATA

| | HYBRID | N | FI | GI | YM | YLD | MST | % SL | % RL | % DE |
|---|---|---|---|---|---|---|---|---|---|---|
| RE | 8543 | 53 | 8.0 | 0.5 | 0.9 | 2.6 | 3.3 | 0.6 | −1.3 | −0.1 |
| RE | 8501 | 36 | 12.5 | 3.8 | 0.9 | −0.4 | 3.8 | 1.8 | −0.0 | 0.9 |

Table 9C shows the advantage of ZS0541/Inbred 2 over 8543 and 8501. ZS0541/Inbred 2 has better G index ratings than 8543 and 8501. ZS0541/Inbred 2 has better yield by moisture and better moisture, stalk lodging than 8543 or 8501. 8501 shows a better yield, and 8543 shows a lower yield than ZS0541/Inbred 2. But, both 8543 and 8501 show at best a 3.0 moisture disadvantage compared with ZS0541/Inbred 2.

TABLE 10A

HYBRID SUMMARY ZS0541/INBRED 2

PATHOLOGY DATA

| HYBRID | HS* | GLS | NLB | CCR** |
|---|---|---|---|---|
| ZS0541/INBRED 2 | 9 | 3 | 5 | 5 |
| 8543 | | 4 | 8 | |
| 8574 | | 3 | 5 | |
| 8501 | | 5 | 8 | |

*HS = head smut
**CCR = common corn rust

Table 10A shows the pathology data for ZS0541/Inbred 2 compared to ICI Seeds' commercial hybrids 8543, 8574, and

TABLE 10B

| INBRED | CCR | GLS | MDMVB | NLB |
|---|---|---|---|---|
| ZS0541 | 7.3 | 6 | 1 | 5 |
| A632 | 4.3 | 3.2 | 3.7 | 5.2 |
| PVP#000065 | 4.5 | 7 | . | 5.2 |
| SGI100 | . | 5 | . | 4.5 |
| ZS0193 | 6 | 3 | 3 | 7 |

Table 10B compares the pathology data of the inbreds. ZS0541 has a superior resistance to common corn rust than the other inbreds. ZS0541 has a better rating than A632, PVP#000065, SGI100 and ZS0193 for gray leaf spot resistance. ZS0541 has little resistance to $MDMV_B$ and intermediate resistance to northern leaf blight.

TABLE 11A

| HYBRID | TESTS | GI | ADV | FI | ADV | YLD | ADV | MOIST | ADV |
|---|---|---|---|---|---|---|---|---|---|
| STATE: COLORADO | | | | | | | | | |
| ZS0541/Inbred 1 RE | 3 | 187 | 7 | 136 | –2 | 184.4 | 17.4 | 22.2 | –3.8 |
| 8574 RE | 3 | 180 | | 138 | | 167.0 | | 18.3 | |
| ST | 19 | 199 | 6 | 157 | 2 | 199.9 | 9.8* | 18.2 | –1.3* |
| ST | 19 | 193 | | 155 | | 190.2 | | 16.9 | |

Table 11A shows the research testing and experimental strip testing data for ZS0541 in Colorado. Colorado soil is often characterized by high pH and low organic matter soil. ZS0541/Inbred 1 evidenced 17.4 bushels to the acre more yield and three points higher moisture than 8574 in research tests in this environment. In experimental strip tests ZS0541/Inbred 1 showed significantly better yield with significantly higher moisture in these Colorado conditions.

TABLE 11B

| HYBRID | TESTS | GI | ADV | FI | ADV | YLD | ADV | MOIST | ADV |
|---|---|---|---|---|---|---|---|---|---|
| STATE: COLORADO | | | | | | | | | |
| ZS0541/Inbred 2 RE | 5 | 186 | 8 | 137 | 5 | 186.3 | 24.1* | 21.2 | –1.0 |
| 8574 RE | 5 | 178 | | 132 | | 162.2 | | 20.2 | |
| ST | 8 | 203 | 9 | 158 | 5 | 206.5 | 17.3* | 19.7 | –1.7 |
| ST | 8 | 194 | | 153 | | 189.2 | | 18.0 | |

ZS0541/Inbred 2 when compared with 8574 in the soils of Colorado also show excellent Western environment performance. In research testing, ZS0541 in hybrid combination showed an advantage of 24.1 bushels per acre over 8574 with a one point higher grain moisture at harvest. Under experimental strip conditions, a significant yield difference of 17.3 bushels per acre more of ZS0541 hybrid was shown with a 1.7 disadvantage in ZS0541 hybrid's grain moisture.

The foregoing is set forth by way of example and is not intended to limit the scope of the invention.

This invention also is directed to methods for producing a corn plant by crossing a first parent corn plant with a second parent corn plant wherein the first or second parent corn plant is an inbred corn plant from the line ZS0541. Further, both first and second parent corn plants can come from the inbred corn line ZS0541. A variety of breeding methods can be selected depending on the mode of reproduction, the trait, the condition of the germplasm. Thus, any such methods using the inbred corn line ZS0541 are part of this invention: selfing, backcrosses, hybrid production, crosses to populations, and the like.

Various culturing techniques known to those skilled in the art, such as haploid, transformation, and a host of other conventional and unconventional methods are within the scope of the invention. All plants and plant cells produced using inbred corn line ZS0541 are within the scope of this invention. The invention encompasses the inbred corn line used in crosses with other, different, corn inbreds to produce (F1) corn hybrid seeds and plants with the characteristics that make good hybrids. This invention includes cells which upon growth and differentiation produce corn plants having the physiological and morphological characteristics of the inbred line ZS0541.

Duncan, from at least 1985–1988 produced literature on plant regeneration from callus. Both inbred and hybrid callus have resulted in regenerated plants at excellent efficiency rates. Somatic embryogenesis has been performed on various maize tissue such as glume which before the 1980's was considered unuseable for this purpose. The prior art clearly teaches the regeneration of plants from various maize tissues.

Stauffer Chemical, the predecessor to Zeneca Ag Chem, in European Patent Application, publication 160,390, incorporated herein by reference describes tissue culture of corn.

Corn tissue culture procedures are also described in the literature as early as 1982.

A deposit of at least 2500 seeds of the inbred seed of of this invention is maintained by ICI Seeds, 2369 330th Street, Slater, Iowa 50244. Access to this deposit will be available during the pendency of this application to the Commissioner of Patents and Trademarks and persons determined by the Commissioner to be entitled thereto upon request. All restrictions on availability to the public of such material are removed upon issuance of the patent. The Applicant made a deposit of at least 2500 seeds of Inbred Corn Line ZS0541 with the American Type Culture Collection (ATCC), located at 12301 Parklawn Drive, Rockville, Md. 20852. The seeds were deposited with the ATCC on Sep. 3, 1996 and were taken from the inbred seed deposit maintained by ICI Seeds. The ATCC deposit will be maintained in that depository, which is a public depository, for a period of 30 years, or 5 years after the last request, or for the effective life of the patent, whichever is longer, and will be replaced if it becomes nonviable during that period. Additionally, Applicant has satisfied all the requirements of 37 C.F.R. §§ 1.801-1.809, including providing an indication of the viability of the sample.

Inbreds designated MBS are available from Mike Brayton Seed in Iowa. Inbreds designated SGI are available from Seed Genetic Inc. in New Jersey. Information on the ZS designations may be available from the PVP office.

Accordingly, the present invention has been described with some degree of particularity directed to the preferred embodiment of the present invention. It should be appreciated, though, that the present invention is defined by the following claims contrued in light of the prior art so that modifications or changes may be made to the preferred embodiment of the present invention without departing from the inventive concepts contained herein.

We claim:

1. Inbred corn seed designated ZS0541, wherein a seed sample of ZS0541 has been deposited under ATCC number 97703.

2. A corn plant produced by the seed of claim 1.

3. A tissue culture of regenerable cells of ZS0541, wherein a seed sample of ZS0541 has been deposited under ATCC number 97703.

4. A corn plant having the genotype of ZS0541 regenerated from the tissue culture of claim 3.

5. Hybrid seed produced by the following method:
   (a) planting seeds of corn inbred lines ZS0541, wherein a seed sample of ZS0541 has been deposited under the ATCC number 97703, and another inbred line;
   (b) preventing pollen production by the plants of one of the inbred lines;
   (c) having pollination occur between said inbred lines wherein hybrid seed is formed; and
   (d) harvesting said hybrid seed.

6. Hybrid seed produced by hybrid combination of plants of inbred corn seed designated ZS0541 according to claim 2 and plants of another inbred line.

7. Hybrid plants grown from seed of claim 6.

8. A first generation (F1) hybrid corn plant produced by the process of:
   (a) planting seeds of corn inbred lines ZS0541, wherein a seed sample of ZS0541 has been deposited under the ATCC number 97703, and another inbred line;
   (b) preventing pollen production by the plants of one of the inbred lines;
   (c) having pollination occur between said inbred lines wherein hybrid seed is formed; and
   (d) harvesting said hybrid seed; and
   (f) growing said harvested seed.

9. A tissue culture of the regenerable cells of the corn plant of claim 7.

10. A tissue culture of the regenerable cells of the corn plant of claim 8.

* * * * *